(12) United States Patent
Wettstein et al.

(10) Patent No.: US 9,927,379 B2
(45) Date of Patent: Mar. 27, 2018

(54) THERMOANALYTICAL SENSOR, AND METHOD OF MANUFACTURING THE SENSOR

(71) Applicant: Mettler-Toledo AG, Greifensee (CH)

(72) Inventors: Paul Wettstein, Mellingen (CH); Markus Bendler, Zumikon (CH)

(73) Assignee: Mettler-Toledo GmbH, Greifensee (CH)

( * ) Notice: Subject to any disclaimer, the term of this patent is extended or adjusted under 35 U.S.C. 154(b) by 363 days.

(21) Appl. No.: 14/660,328

(22) Filed: Mar. 17, 2015

(65) Prior Publication Data

US 2015/0268182 A1   Sep. 24, 2015

(30) Foreign Application Priority Data

Mar. 18, 2014   (EP) .................................... 14160420

(51) Int. Cl.
*G01N 25/48* (2006.01)
*H05K 1/11* (2006.01)
(Continued)

(52) U.S. Cl.
CPC ......... *G01N 25/4833* (2013.01); *G01K 17/00* (2013.01); *H05K 1/11* (2013.01);
(Continued)

(58) Field of Classification Search
CPC ...... G01K 17/00; G01N 25/4833; H05K 1/11; H05K 2201/10151; H05K 2201/10287; H05K 3/4046
See application file for complete search history.

(56) References Cited

U.S. PATENT DOCUMENTS 2,983,888 A * 5/1961 Wormser ................. G01J 5/20
338/18
3,693,011 A * 9/1972 De Vaux ................. G01J 5/20
250/336.1
(Continued)

FOREIGN PATENT DOCUMENTS

JP   2003-315164 A   11/2003

OTHER PUBLICATIONS

Neher, C., et al. "Further developments in gold-stud bump bonding." Journal of Instrumentation 7.02 (2012): C02005.*
(Continued)

*Primary Examiner* — Lisa Caputo
*Assistant Examiner* — Punam Roy
(74) *Attorney, Agent, or Firm* — Standley Law Group LLP (57) ABSTRACT

A thermoanalytical sensor has a substrate, a measurement position, a temperature sensor unit, and an electrical contact pad. The temperature sensor unit senses the temperature at the measurement position. It is connected via the electrical contact pad to a metallic wire and thereby tied into an electronic circuit. The substrate is prepared with at least one measurement position, at least one temperature sensor unit and at least one electrical contact pad on a top side of the substrate. A passage in the substrate allows connection to the electrical contact pad. A metallic wire is inserted into the passage from the bottom side of the substrate and melted into a small ball on the upper end of the wire. A materially integral connection as a bonded joint between the upper end of the metallic wire and the electrical contact pad is made by applying pressure and heat to the metal ball.

19 Claims, 5 Drawing Sheets

(51) Int. Cl.
  *G01K 17/00*  (2006.01)
  *H05K 3/40*   (2006.01)

(52) U.S. Cl.
  CPC . *H05K 3/4046* (2013.01); *H05K 2201/10151* (2013.01); *H05K 2201/10287* (2013.01); *Y10T 29/4913* (2015.01)

(56) References Cited

U.S. PATENT DOCUMENTS

| | | | |
|---|---|---|---|
| 3,732,722 A * | 5/1973 | Norem | G01N 25/486 374/12 |
| 4,133,208 A * | 1/1979 | Parlanti | G01K 1/028 341/167 |
| 4,640,629 A * | 2/1987 | Antonini | G01J 5/20 29/612 |
| 5,033,866 A | 7/1991 | Kehl et al. | |
| 5,528,080 A * | 6/1996 | Goldstein | H01L 21/76879 257/621 |
| 5,721,430 A * | 2/1998 | Wong | G01N 21/3504 250/338.5 |
| 5,842,788 A | 12/1998 | Danley et al. | |
| 6,318,890 B1 * | 11/2001 | Hutter | G01N 25/4846 374/1 |
| 6,390,669 B1 * | 5/2002 | Nakamura | G01N 25/4866 374/10 |
| 6,508,585 B2 * | 1/2003 | Nakamura | A61K 31/203 374/10 |
| 6,583,391 B2 * | 6/2003 | Jorimann | G01N 25/4833 219/494 |
| 6,935,776 B2 | 8/2005 | Hütter | |
| 7,258,482 B2 | 8/2007 | Hütter | |
| 7,371,676 B2 | 5/2008 | Hembree | |
| 7,473,029 B2 * | 1/2009 | Hutter | G01K 7/02 136/225 |
| 7,588,367 B2 | 9/2009 | Huetter et al. | |
| 7,674,655 B2 * | 3/2010 | Chua | H01L 21/561 438/126 |
| 7,682,962 B2 | 3/2010 | Hembree | |
| 7,728,443 B2 | 6/2010 | Hembree | |
| 7,757,385 B2 | 7/2010 | Hembree | |
| 7,919,846 B2 | 4/2011 | Hembree | |
| 8,053,909 B2 | 11/2011 | Hembree | |
| 9,013,044 B2 * | 4/2015 | Wood | H01L 24/11 257/774 |
| 9,039,280 B2 * | 5/2015 | Peroulis | G01K 7/34 374/183 |
| 2007/0126091 A1 * | 6/2007 | Wood | H01L 23/3114 257/669 |
| 2014/0247106 A1 | 9/2014 | DeFrietas et al. | |
| 2014/0355643 A1 * | 12/2014 | Sharratt | G01K 17/00 374/1 |
| 2014/0371744 A1 | 12/2014 | Dekker et al. | |

OTHER PUBLICATIONS

Wang, Quan, et al. "A simple thermo-compression bonding setup for wire bonding interconnection in pressure sensor silicon chip packaging." Microsystem technologies 17.10-11 (2011): 1629-1633.*

Lum, I., M. Mayer, and Y. Zhou. "8-Microelectronics wire bonding." Microjoining and Nanojoining, Woodhead Publishing Series in Welding and Other Joining Technologies (2008): 205.*

Moffat, Robert J., "Thermocouple Basics" pp. 1-10. Sep. 3, 2008. Accessed online on May 1, 2017 at <http://wwwcourses.sens.buffalo.edu/mae334/notes/ThermocoupleBasics.pdf>.*

Ventura, Guglielmo, and Mauro Perfetti. "How to Measure Heat Capacity at Low Temperatures." Thermal Properties of Solids at Room and Cryogenic Temperatures. Springer Netherlands, 2014. 39-67.*

Wilson, Scott, et al. "Fabrication and testing of a thin-film heat flux sensor for a stirling convertor." 7th International Energy Conversion Engineering Conference. 2009.*

Eder, F.X., Arbeitsmethoden der Thermodynamik, Band 2 (Working Methods of Thermodynamics, vol. 2), Springer Verlag, 1983, p. 240.

* cited by examiner

Fig. 8

THERMOANALYTICAL SENSOR, AND METHOD OF MANUFACTURING THE SENSOR

CROSS-REFERENCE TO RELATED APPLICATIONS

This application is entitled to benefit of a right of priority under 35 USC § 119 from European patent application 14160420.7, filed on 18 Mar. 2014, the content of which is incorporated by reference as if fully recited herein.

TECHNICAL FIELD

The disclosed invention concerns a thermoanalytical sensor and a method of manufacturing the sensor.

BACKGROUND

Thermoanalytical sensors are used in suitably designed thermal analysis instruments for the determination of different properties and parameters of a sample that is subjected to changes in temperature.

Examples of state-of-the-art thermal analysis instruments include, among others, DSC (differential scanning calorimetry) instruments. DSC instruments are used to determine temperature-dependent changes in the chemical or physical properties of a sample, or rather of the material from which the sample was taken. This includes for example heat-flow measurements of exothermic or endothermic events accompanying a transition, such as for example a phase transition, as well as other effects occurring in a sample that is subjected to temperature changes. The changes taking place in the sample can be determined through comparison against a reference, wherein the latter can be either the unoccupied reference measurement position or a suitable reference material. Dependent on the type of DSC instrument, the reference material or the sample material can be placed on the respective measurement position either directly or in a suitable receptacle. Thermoanalytical sensors can also be employed in other instruments such as for example TGA-DSC instruments (wherein TGA stands for Thermo-Gravimetric Analysis), or HP-DSC (High-Pressure DSC) instruments, as well as in further instruments of the known state of the art.

Thermal analysis instruments are frequently run in a heat flux operating mode and in a power compensation operating mode.

In the power compensation mode, the power supplied to a heater and/or the power supplied to a compensation heater is controlled and regulated in such a way that the temperature difference between the reference position and the sample position is driven to zero. Based on the power needed for this compensation, it is possible to deduce the heat flow into the sample. In the ideal case, the spent power corresponds to the heat flow into the sample.

The heat flux principle is often used in thermal analysis instruments that have a common holder for the sample and the reference. The heat flow paths between the measurement positions and the heater should be known so that, ideally, any temperature differences between the two measurement positions are only the result of changes in the sample. Based on the real temperatures at the sample position and at the reference position, the heat flow rates can be calculated and quantitatively evaluated.

Thermoanalytical sensors for instruments of this type are often disk-shaped, with one surface carrying at least one measurement position that is connected to a temperature sensor unit which senses the temperature at the respective measurement position and/or the differential temperature between a sample position and a reference position. From a connected heater device, the sensor and the at least one measurement position associated with the sensor can be supplied with heat, in particular according to a suitable temperature/time program for the generation of temperature changes.

The known state of the art offers different types of such thermoanalytical sensors.

For example in F. X. Eder, Arbeitsmethoden der Thermodynamik, Band 2 (Working Methods of Thermodynamics, Volume 2), Springer Verlag 1983, page 240, a sensor is disclosed which includes a temperature sensor unit produced by thin-film vapor deposition on a substrate.

In DE 39 16 311 C2, a sensor is disclosed with a temperature sensor unit deposited on a substrate by using thick film technology methods.

These sensors have in common that the temperature sensor units have at each measurement position a plurality of thermocouples or thermal junctions that are formed directly on a sensor surface.

Sensors with temperature sensor units containing a plurality of thermocouples are also disclosed in EP 1 528 392 A1, DE 10 227 182 A1, DE 39 16 311 A1 and WO 2006/114394 A1. The sensors disclosed in these references have one or more measurement position, wherein the temperature sensor units have been deposited on the sensor surface by using different deposition techniques and/or different layout patterns, for example in order to increase the number of thermocouples at each measurement position, or to provide the capability of measuring temperature in more dimensions with an arrangement of thermocouples in several layers or planes of the sensor.

These sensors have in common that each measurement position is connected with a temperature sensor unit which is formed in this case in particular as a thermocouple arrangement deposited in thin film or thick film technology in a pattern surrounding the measurement position on the top side of a substrate. Each thermocouple arrangement is connected to an electronic circuit by way of an electrical contact pad and at least one suitable wire passing through the substrate. One end of the metallic wire, the upper end, is bonded from the top side of the substrate to the electrical contact pad of the temperature sensor unit in order to establish a materially integral connection in the form of a bonded joint between the electronic circuit and the temperature sensor, wherein with the fastening of each individual wire, a wire loop is created on the top side of the substrate.

The connection to the circuit by bonding the at least one metallic wire from above, i.e. from the top side of the sensor, with each wire forming a loop, has the disadvantage that it strongly limits the total number of connections or contacts that can be realized, as the space on the top side of the sensor becomes filled up with the wire loops. In addition, the wire loops can easily be damaged and/or torn apart, whereby the sensor becomes inoperative.

It is therefore an unmet object of the prior art to provide a particularly robust and user-friendly sensor which, in addition, is designed so that a multitude of contacts can be arranged on the top side of the sensor.

SUMMARY

This task is solved by a method of manufacturing a thermoanalytical sensor and by a thermoanalytical sensor that is manufactured according to the inventive method and includes a substrate with a top side and an underside, at least one measurement position, at least one temperature sensor unit, and at least one electrical contact pad. The at least one measurement position, the at least one temperature sensor unit and the electrical contact pad are arranged on the top side of the sensor, with the temperature sensor unit measuring the temperature at the measurement position. The temperature sensor unit is connected by way of the electrical contact pad to a metallic wire and thereby tied into an electronic circuit. The method covers the following steps: After the substrate has been prepared, at least one measurement position, at least one temperature sensor unit and at least one electrical contact pad are produced on the top side of the substrate. In addition, at least one passage is made in the substrate for the connection to the electrical contact pad. Next, a metallic wire is inserted into the passage from the underside of the substrate, and the upper end of the wire which protrudes at the top side of the substrate is melted and thereby takes on the form of a small metal ball. The bond is completed in the form of a materially integral connection between the upper end of the metallic wire and the electrical contact pad. To form this connection, the metal ball is fused to the contact pad through the application of pressure and heat, whereby the wire is bonded to the contact pad.

This kind of bonding is particularly advantageous for thermoanalytical sensors, as the formation of undesirable wire loops at the top side of the sensor can thus be avoided. The bonded connection on the top side of the sensor has the form of a compact metallic protuberance which is very smooth and presents no obstacles when placing a sample on the sensor or removing the sample from the sensor. The temperature sensor unit is preferably bonded or connected to two metallic wires by way of two contact pads through the formation of two bonded connections.

Through the electrical contact pad and a metallic wire, the temperature sensor unit can be tied into an electronic circuit.

The method can further cover the process of forming two or more measurement positions and two or more temperature sensor units on the top side of the sensor, wherein an individually dedicated temperature sensor unit is assigned to each measurement position.

In addition, this production method is very suitable for the manufacture of sensors with a large number of measurement positions, contact pads for the tapping of sensor signals used to determine different parameters such as e.g. temperature, differential temperature between the measurement positions, pressure, moisture and/or flow rate and/or for the application of a voltage, for example to supply resistance heaters, and/or to run the sensors, as the resultant bonded connections take up much less space, which makes it possible to arrange a larger number of bonded connections on the sensor. Thus, two to three times as many bonded connections, and in particular even five times as many bonded connections, can be arranged on a thermoanalytical sensor of the same diameter.

The temperature sensor unit can be configured as a thermocouple arrangement with at least two thermocouples that are formed in one or more sensor layers on the top side of the sensor. The temperature sensor unit can also include one or more resistance-based temperature sensors such as for example Pt-100 sensors.

As a further part of the method, at least one heating resistor and at least one further electrical contact pad can be formed on the top side of the sensor, as well as a further passage through the sensor, wherein the heating resistor, which serves to heat the at least one measurement position, is connected by way of the electrical contact pad and a further metallic wire to an electrical power supply source, and wherein a materially integral connection in the form of a bonded joint is formed between the electrical contact pad and a metal ball that is formed at the upper end of the further metallic wire. Preferably, the heating resistor is bonded by way of two contact pads to two metallic wires.

Thus, the method is particularly suitable for the production of sensors with different elements that are arranged on the top side of the sensor and have to be electrically connected.

The temperature sensor unit, the heating resistor and/or the electrical contact pad are preferably produced in thick film or thin film technology on the top side of the sensor.

The metallic wires which are used for the bonding include preferably at least one of the following metals or their alloys: gold, palladium, and copper. Due to their material properties, these metals or alloys are particularly advantageous for the forming of the metal ball and the subsequent bonding to the contact pad.

The metallic wire can have a diameter approximately between 0.01 mm and 0.25 mm, in particular a diameter of about 0.1 mm.

The metal ball is preferably formed with a diameter measuring one to five times the wire diameter. The size of the metal ball can be very accurately controlled by way of the experimental conditions. For a gold wire with a diameter of 0.1 mm, forming the ball requires a spark discharge of about 2 to 5 kV.

The electronic circuit of the thermoanalytical sensor can be designed so that the sensor can be used for DSC measurements according to the principle of power compensation and/or according to the heat flux principle.

The invention further covers a thermoanalytical sensor manufactured in accordance with the method described above, in particular a DSC sensor having a substrate with a top side and an underside, wherein at least one measurement position, one temperature sensor unit and at least one electrical contact pad are formed on the top side. The temperature sensor unit detects the temperature of the measurement position. By way of the electrical contact pad the temperature sensor unit is connected to at least one metallic wire and thereby tied into an electronic circuit. The metallic wire enters from the underside of the substrate into a passage that is formed in the substrate. At its upper end, the wire is terminated by a metal ball which, through the application of pressure and temperature, forms a materially integral connection in the form of a bonded junction between the upper end of the metallic wire and the electrical contact pad.

The sensor can further include at least one heating resistor and at least one further electrical contact pad which are formed on the top side of the sensor, wherein the heating resistor, which serves to heat the at least one measurement position, is connected by way of the electrical contact pad and a further metallic wire to an electrical power supply source.

The substrate can include a conductive or a non-conductive material such as for example metals or ceramics. Examples of conductive materials include, among others, steel and/or other hard metals. Non-conductive materials that can be employed include for example the following materials or mixtures thereof: aluminum oxide, steatite, aluminum nitrite, and glass ceramics.

Furthermore, the substrate is of an essentially disk-shaped configuration and has an essentially planar top side on which the at least one measurement position is formed.

BRIEF DESCRIPTION OF THE DRAWINGS

In the following, the method of the invention as well as different examples of thermoanalytical sensors produced in accordance with the method will be described in more detail with references to the drawings, wherein elements that are identical from one drawing to another are identified by the same or similar reference symbols, and wherein.

DETAILED DESCRIPTION OF THE PREFERRED EMBODIMENTS

Figure 1:
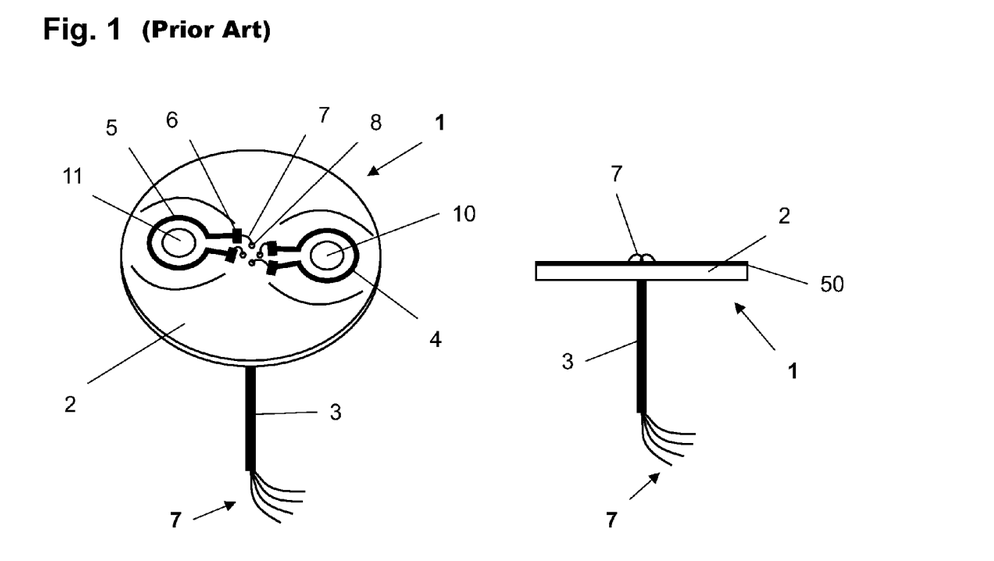
FIG. 1 shows a thermoanalytical sensor of the prior art with two measurement positions, shown in a three-dimensional view and in a side view.

FIG. 1 schematically illustrates a state-of-the-art thermoanalytical sensor 1 in a three-dimensional view and in a side elevation. The thermoanalytical sensor 1 has a disk-shaped substrate 2, for example of a ceramic material, with a top side and an underside. The topside carries two measurement positions 10, 11 and two temperature sensor units 4, 5 which are only schematically indicated here. The temperature sensor units 4, 5 are laid out with each temperature sensor in essence concentrically surrounding the respective measurement position 10, 11, so as to allow a temperature change to be measured with the highest possible accuracy. The temperature sensor unit 4, 5 of a measurement position 10, 11 can for example include a large number of thermocouple junctions which are serially combined into a thermocouple arrangement. These thermal junctions or thermocouples can be deposited on the substrate 2 using either thick film or thin film technology, indicated in the side view as film layer 50. Furthermore, each of the temperature sensor units 4, 5 includes a contact pad 6 which, as shown here, is connected to a thin metallic wire 7 running through a passage 8 in the substrate 2 to the underside of the substrate 2. All metallic wires 7 are sheathed in a sleeve 3 which has the form of a shaft protruding from the underside of the substrate 2. The sleeve 3 is preferably configured with a plurality of capillary conduits, so that the metallic wires can be kept insulated against each other. The free ends of the wires 7 exiting from the sleeve 3 are tied into an electronic circuit (see FIG. 2), so that the temperature sensor units 10, 11 can be connected to a suitable controller device through which the measurement data can be read. The metallic wires 7 in this arrangement can be tied into a common circuit or also into separate circuits.

In the side view which is also shown in FIG. 1, it is clearly evident that each of the metallic wires 7 forms a loop between the contact pad and the passage 8. In practice, this loop has been found very disadvantageous, as this part of the metallic wire 7 can easily be damaged or even torn off when a sample or a sample container is set in place or removed, which can lead to a loss of function or even destruction of the sensor 1.

Figure 2:
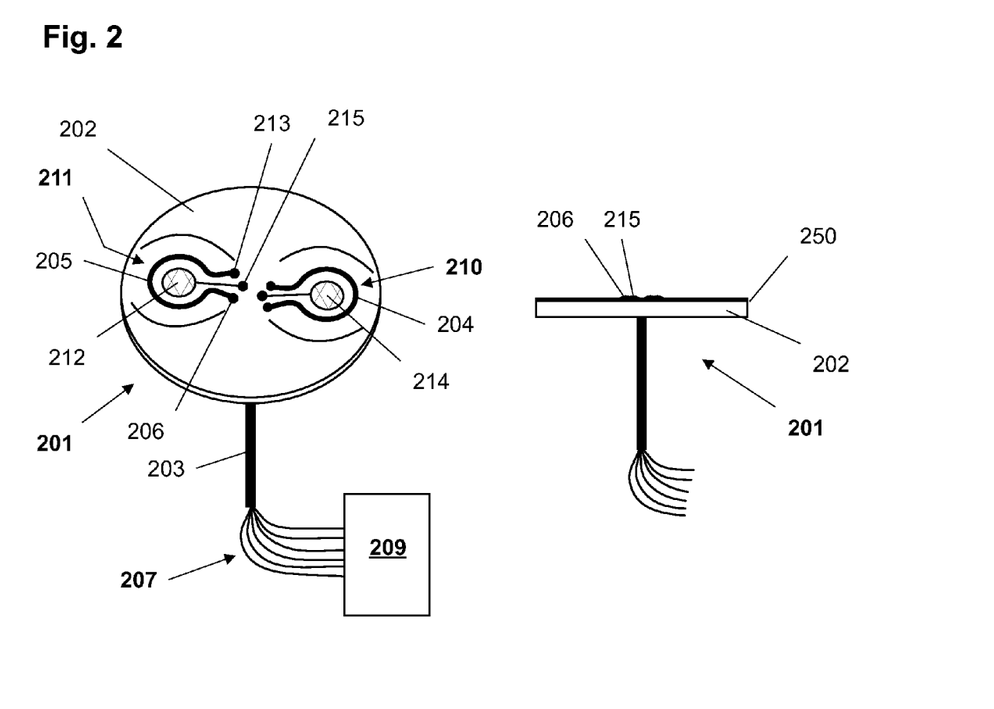
FIG. 2 shows a thermoanalytical sensor of the inventive concept with two measurement positions, shown in a three-dimensional view and in a side view.

FIG. 2 represents a schematic three-dimensional view as well as a side view of a sensor 201 according to the invention, which likewise includes a substrate 202 and two measurement positions 210, 211 arranged on the substrate.

Each of the measurement positions 210, 211 includes a temperature sensor unit 204, 205 as well as a heating resistor 212, 214, which can serve for example as compensation heater when the sensor is operated in power compensation mode. In this example, too, the temperature sensor units 204, 205 consist of a large number of thermocouples which are serially connected into a thermocouple arrangement.

The heating resistors 212, 214 as well as the temperature sensor units 204, 205 are formed on the top side of the substrate 202 in thick film or thin film technology, indicated as a layer 250, wherein each of the heating resistors and temperature sensor units includes a contact pad 206, 213, 215. As already described in the context of FIG. 1, these elements by way of their respective contact pads 206, 213, 215 and suitable metallic wires, are tied into one or more electronic circuits 209. The electrical contact between the contact pads 206, 213, 215 and the respective wires 207 is again established by bonding, but without forming a loop on the top side of the substrate. After the metallic wires 207 have been connected to them, the contact pads 206, 215 present themselves in side view as slight protuberances.

Figure 3A:
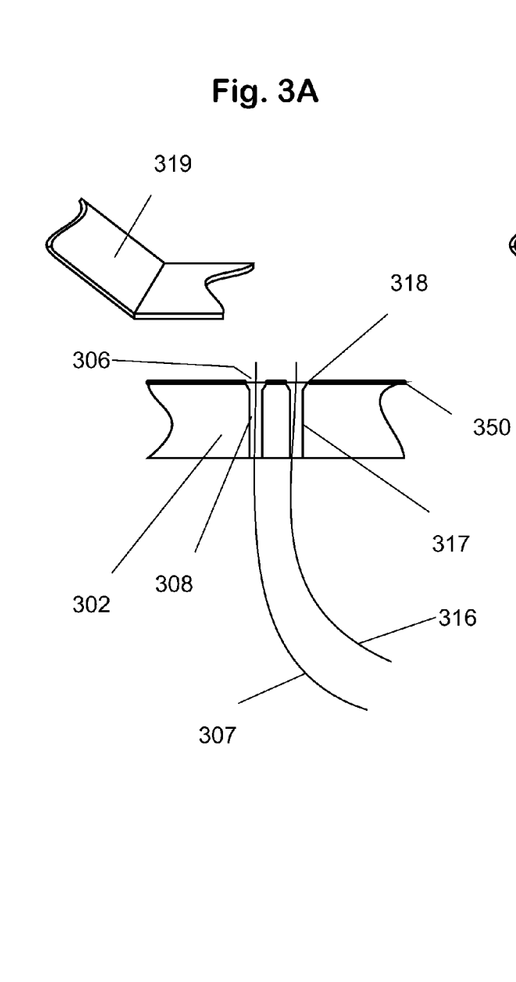
FIG. 3A shows a schematic detail illustration of the thermoanalytical sensor with two electrical contact pads in sectional view with: metallic wires inserted.
Figure 3B:
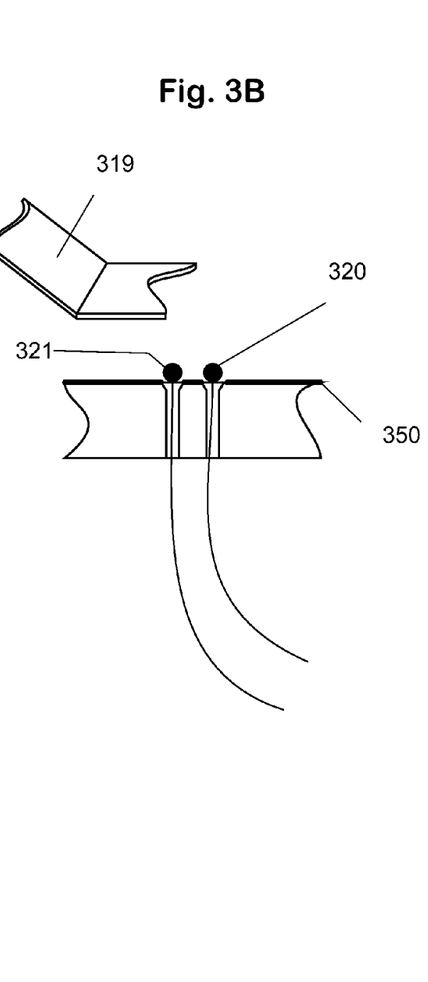
FIG. 3B shows a schematic detail illustration of the thermoanalytical sensor with two electrical contact pads in sectional view with metallic wires inserted and metal balls formed at the wire ends.
Figure 3C:
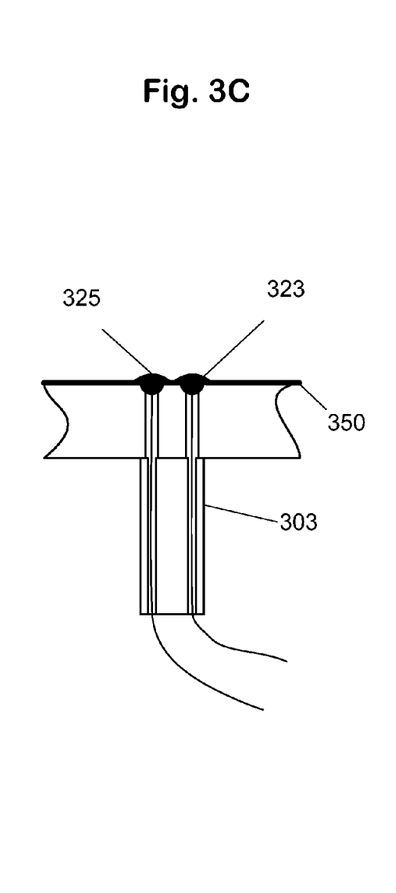
FIG. 3C shows a schematic detail illustration of the thermoanalytical sensor with two electrical contact pads in sectional view with materially integral connections between the electrical contact pads and the metallic wires.

The method of producing this kind of thermoanalytical sensor according to the invention, with a substrate 302 carrying a layer 350 containing among other features at least one contact pad deposited in thin film or thick film technology, at least one measurement position and at least one temperature sensor unit, is illustrated schematically in FIGS. 3A to 3C.

As shown in FIG. 3A, the substrate 302 has two passages 308, 317 into which metallic wires 307 and 316, respectively, are inserted from the underside of the sensor. With a suitable tool 319 and controlled temperature conditions, the upper end of each wire 307, 316 is melted into a ball 320, 321 (see FIG. 3B). Preferably, this process is performed by applying electrical energy.

To form a metal ball with a diameter of about 0.4 mm at the upper end of a wire with a thickness of about 0.1 mm requires a spark discharge of about 2 to 5 kV, if the wire consists essentially of gold. The required voltage needs to be matched to the material of the wire, its thickness, as well as the desired ball diameter. The metallic wire preferably includes one of the following metals and/or alloys thereof: gold, palladium, copper. It is particularly preferred to use a wire consisting essentially of gold.

In a further step, the metal balls 321, 320 which have been produced according to the foregoing description are brought to the melting point under the influence of pressure and temperature and pressed against the contact pad, so that a materially integral connection is formed between the metallic wire 316, 307 (see FIG. 3C) and a contact pad of a temperature sensor unit (see FIG. 2) that is located on the top side of the substrate 302. The wire 307, 316 is now bonded to the contact pad 323, 325. A bonding method of this kind is also referred to as thermocompression bonding. The wires 307, 316 exiting at the underside of the substrate 302 are subsequently trimmed to the desired length and enclosed with a sleeve 303. The sleeve 303 is preferably configured with a plurality of capillary conduits in which the metallic wires are kept electrically and thermally insulated from each other.

For a wire with the dimensions described above, compression forces in an approximate range from 10 to 100 N and temperatures of about 300° C. are needed to produce the materially integral connection, with the required temperature being dependent on the material of the wire.

FIGS. 4 to 7 show different examples of thermoanalytical sensor according to the invention in plan view.

Figure 4:
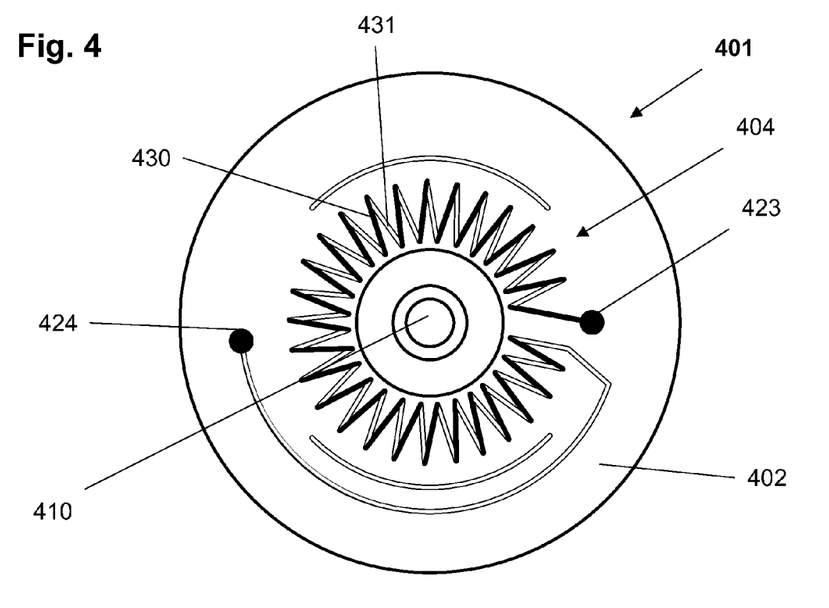
FIG. 4 represents a top view of a first thermoanalytical sensor with one measurement position.

FIG. 4 shows a sensor 401 with a single measurement position 410 on the top side of a substrate 402 which is enclosed by a temperature sensor unit 404 of a star-shaped layout. The temperature sensor unit 404 consists of a large number of thermocouples 430, 431 of two different thermocouple materials which have been deposited on the substrate 402 in alternating sequence. At each of the points where the two thermocouple materials meet, a thermocouple junction is formed. At both ends, the temperature sensor unit 404 is bonded by way of contact pads 423 and 424, respectively, to metallic wires which are not visible in this plan view. Similar temperature sensor units are disclosed for example in EP 0 990 893 A1.

Figure 5:
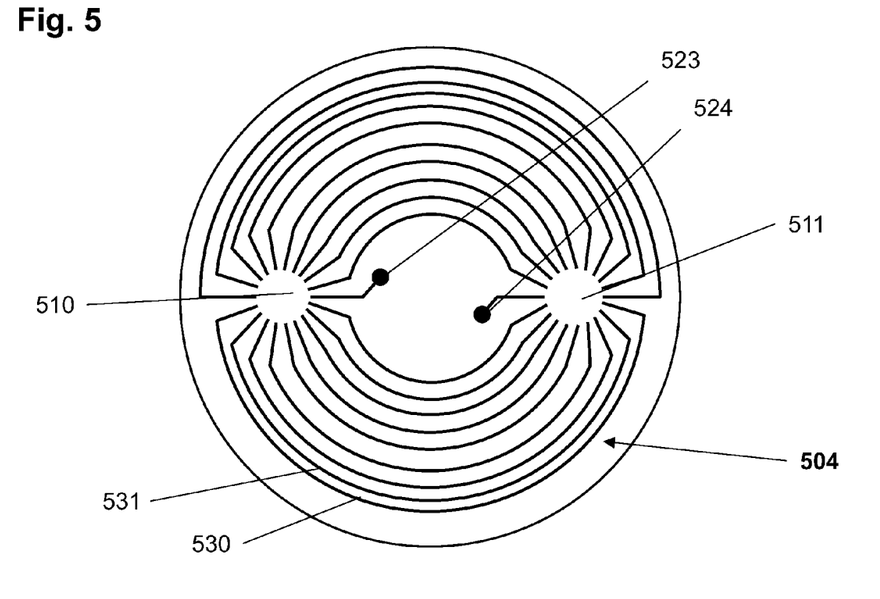
FIG. 5 represents a top view of a second thermoanalytical sensor with two measurement positions.

FIG. 5 shows a further example of a thermoanalytical sensor with two measurement positions 510, 511 formed on a substrate 502.

The substrate 502 is an essentially circular disk which consists of one of the materials described above. On its top side, the substrate carries a temperature sensor unit which has been produced in thick film technology and is composed of a large number of individual, serially connected thermocouples 530, 531—twenty in this example—, each of which consists of two different precious metals. The thermocouples 530, 531 are arranged to form circles around the two measurement positions 510, 511, with contact pads 523, 524 arranged, respectively, at the ends of the temperature sensor unit 504 next to the two measurement positions 510, 511. Through the contact pads and suitable metallic wires that are bonded to them, the temperature sensor unit 504 is tied into an electronic circuit. Between the measurement positions 510, 511, the thermocouples 530, 531 form semicircles, which can be smoothly curved as shown here or which could also be of a polygonal configuration. The thermocouples 530, 531 are arranged at a sufficient distance from each other, so that they can run parallel to each other while maintaining sufficient insulation between them. On their outward-facing side or top side, the thermocouples 530, 531 are preferably covered by an electrically insulating coating layer (not shown in the drawing), which can for example be transparent and can extend over the entire top surface of the thermocouple sensor. Further embodiments of thermoanalytical sensors of this type are described for example in DE 39 163 11 A1.

Figure 6:
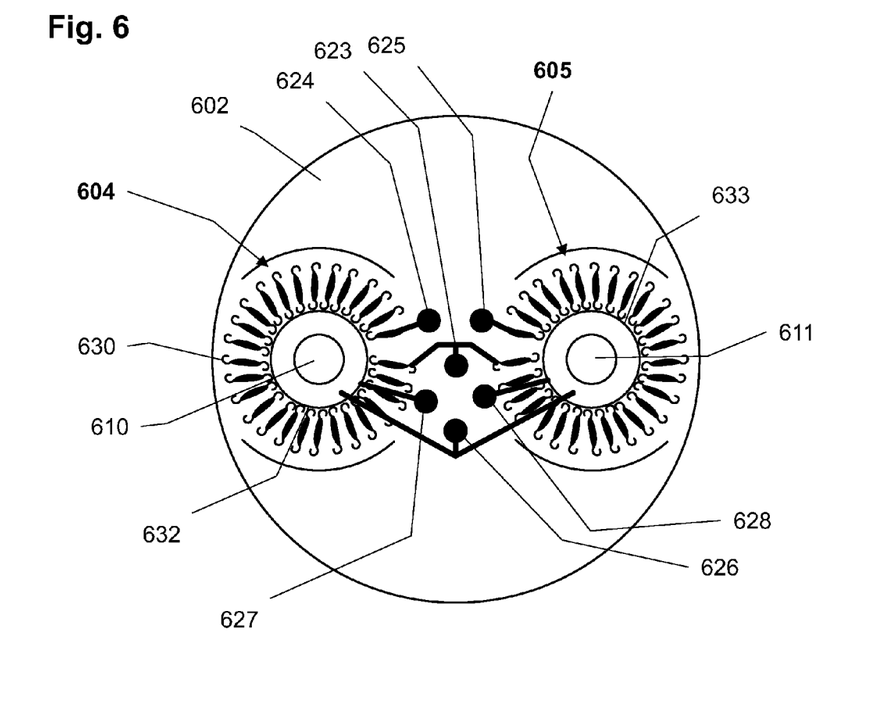
FIG. 6 represents a top view of a third thermoanalytical sensor with two measurement positions.

FIG. 6 shows a further embodiment of a thermoanalytical sensor in plan view. A temperature sensor unit 604 which is deposited in thick film technology on the top side of a disk-shaped ceramic substrate 602 serves to produce measurement signals that are suitable for the practice of differential thermal analysis. The measurement positions 610, 611, which can also be referred to as sample position 610 and reference position 611 lie on a diameter of the circular substrate at equal radial distances from the center point. The measurement position 610 is surrounded by a thermopile of serially connected thermocouples 630. Each of the thermocouples 630 consists of two different thermocouple materials which extend in the form of rectilinear traces in an approximately radial direction between the measurement locations or thermocouple junctions at both terminations of the traces, so that the measurement locations are arranged alternatingly at a smaller and a larger radial distance from the center of the measurement position 610. Furthermore, inside the inner of the two circles formed by the thermocouples 630 a first thermocouple material 632 is arranged on the substrate 602 in the shape of a ring that concentrically surrounds the measurement position 610. The second measurement position 611, i.e. the reference position has an essentially identical layout as the first measurement position 610 and equipped with a further temperature sensor unit 605.

Two electrically equivalent terminations of the two temperature sensor units 604, 605 are tied together at a contact pad 623 which is formed on the substrate 602. Each of the two other terminations is connected by a connector trace to a further contact pad 624, 625. The contact pads 623, 624, 625 are bonded, as described above, to suitable metallic wires which run through passages lying, respectively, below the contact pads 623, 624, 625 and which exit from the underside of the substrate 602. The wires serve to tie the temperature sensor devices into an electronic circuit, for example for the purpose of detecting the temperature measurement signals.

Additionally, the substrate 602 carries a further circuit structure of two contact pads 627, 628 which are laid out mirror-symmetrically between the two measurement positions 610, 611. Connector traces extend likewise mirror-symmetrically and in approximately radial directions from the contact pads 627, 628 to the first thermocouple material 632, 633, establishing an electrical connection between the latter and the contact pads 627, 628. The insulation required between this contact pad structure and the thermocouple circuit structures traversed by it is taken into account in the thick film production process.

Also arranged on the substrate 602 is a further shared contact pad 626. A connector trace runs from the contact pad 626 to a Y-shaped junction, where it bifurcates into mirror-symmetric branches that extend into the ring-shaped first thermocouple materials 632, 633, bridging over the two temperature sensor units, from which the branch traces are separated by an insulating layer. The connector and branch traces consist of a second thermocouple material which forms thermocouples with the first thermocouple materials 632, 633, respectively. The signal occurring at these thermocouples can be tapped between the shared contact pad 626 and the contact pads 627, 628, respectively, as absolute temperature signal. Further embodiments of temperature sensor units of this kind are described for example in DE 10 227 182 A1.

Figure 7:
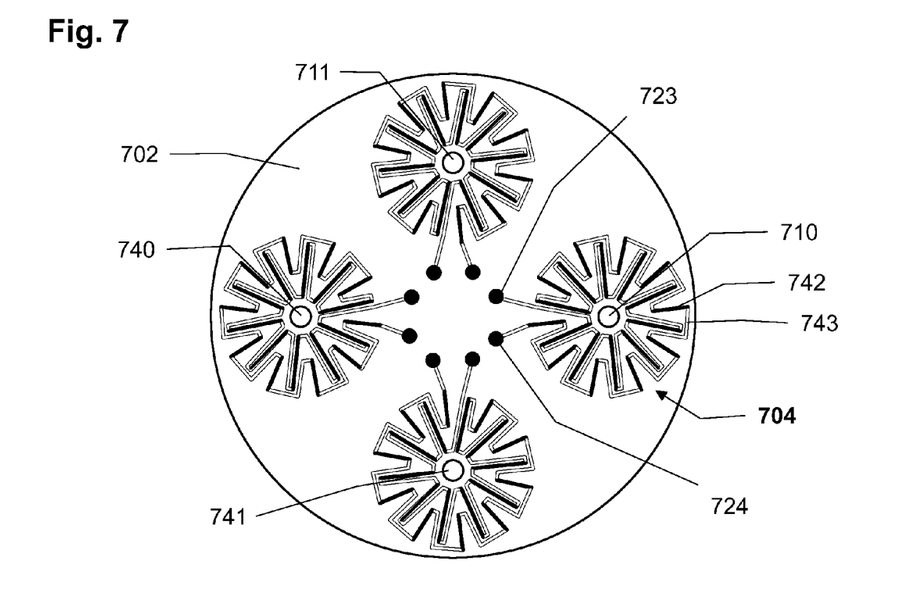
FIG. 7 represents a top view of a fourth thermoanalytical sensor with four measurement positions.

In FIG. 7, a further embodiment of a thermoanalytical sensor with four measurement positions 710, 711, 740, 741 arranged on a substrate 702 is illustrated in plan view.

The measurement positions 710, 711, 740, 741 are essentially equivalent and will be described through the representative example of the position 710.

The substrate 702 is again disk-shaped and consists of one of the materials described above. The measurement position 710 includes a temperature sensor unit 704 deposited in thick film technology. The temperature sensor unit is composed of a large number of thermocouples 742, 743 which consist of two different thermocouple materials that have been deposited on the substrate 402 in alternating trace segments. The thermocouples 742, 743 are laid out in a double star pattern, so that the temperature sensor unit 704 surrounds the measurement position 710 with measurement points that are located on four concentric circles enclosing the measurement position. This layout of the thermocouples is particularly advantageous as it can accommodate a large number of measurement points.

The thermocouples are connected in series and end at two contact pads 723, 724 in the central area of the substrate 702. The contact pads 723, 724 are bonded, as described above, to suitable metallic wires which run through passages from the underside of the substrate 702. Further embodiments of temperature sensor units of this kind are described for example in EP 1 528 392 A1.

As is evident from FIG. 6 as well as from FIG. 7, a thermoanalytical sensor according to the invention is very advantageous, as all of the contact pads can be arranged relatively close to each other in the central area of the sensor, even leaving space for further contact pads and thus also for sensors with further electronic elements and/or allowing more than four measurement positions on the substrate to be realized. As previously described, the circuit structures on the top side of the thermoanalytical sensors can be realized in thick film or thin film technology. As a further possibility, the substrate can be produced using the so-called LTCC (Low Temperature Co-Fired Ceramics) technology.

In the LTCC process, plates of a ceramic material are stacked on top of each other in the so-called green state and sintered together, so that a uniform structure is produced as a result. Each individual plate can be worked on or printed on in the green state, so that a temperature sensor unit that has been deposited in thin film or thick film technology, or other electronic elements, can be realized through a configuration with a plurality of strata or layers of the finished sensor. On the one hand, this allows a much larger number of measurement points to be arranged around an individual measurement position. In addition, it even opens the way to producing three-dimensional temperature sensor arrangements. Sensors of this type of construction can likewise be electrically contacted by using the bonding process described above. Examples of thermoanalytical sensors with temperature sensor units produced by the LTCC process are disclosed for example in EP 1 875 181 A1.

Figure 8:
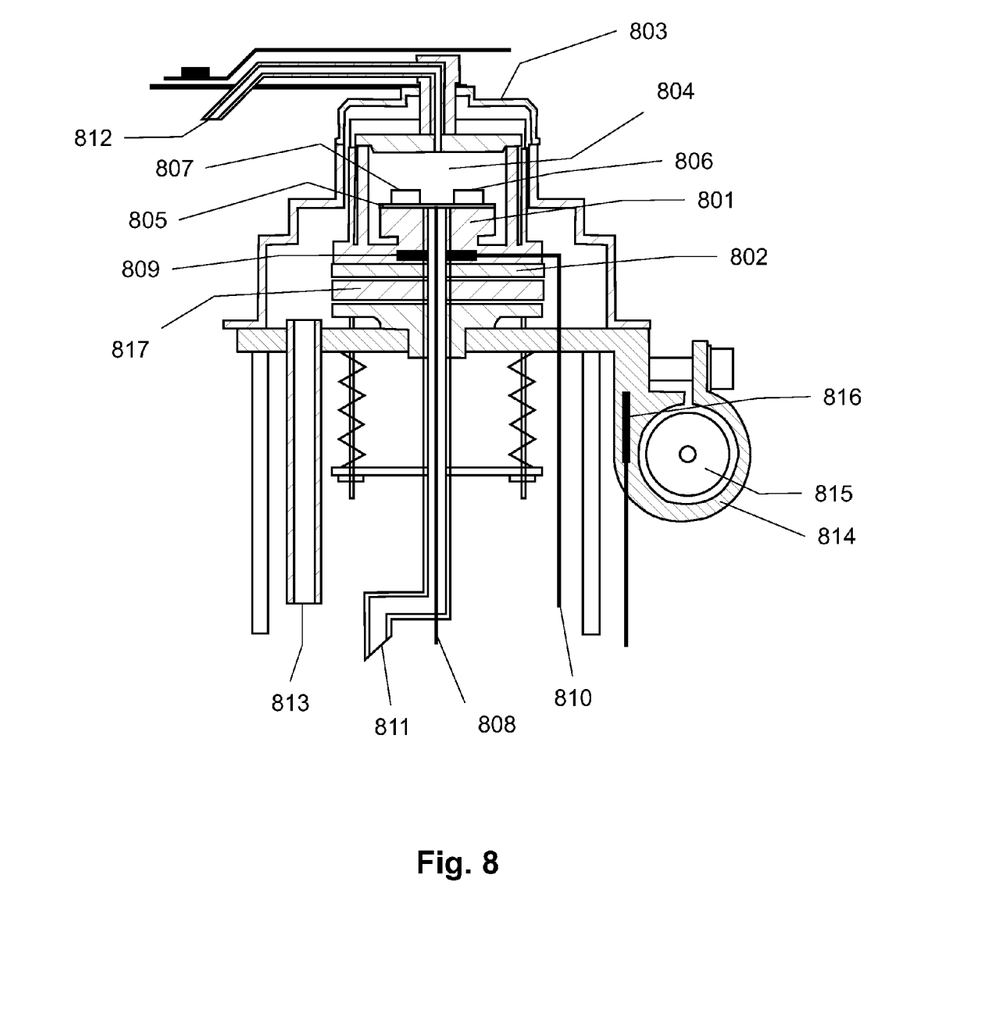
FIG. 8 represents a schematic illustration of a differential calorimeter with a thermoanalytical sensor having the inventive concept.

FIG. 8 represents a schematic view in a vertical section plane through a DSC instrument in which a thermoanalytical sensor according to the invention can be used. The DSC instrument includes a hollow cylindrical furnace block 801 of silver, which can be heated by a flat resistance heater 802. The furnace block 801 is closed off at its upper end by a cover arrangement 803 which can be taken off in order to allow access to the interior 804 of the furnace block 801 for placing samples inside.

A thermoanalytical sensor with a disk-shaped substrate 805 that is thermally coupled to the furnace block 801 extends in the interior space 804 of the furnace block.

The horizontal radial plane on the top side of the disk-shaped substrate 805 carries a first measurement position for a sample crucible 806 and a second measurement position arranged in thermal symmetry to the first measurement position and serving as reference position which, as shown here, can serve as a seat for a reference crucible 807. The positions of the sample crucible 806 and the reference crucible 807 each include a temperature sensor unit. In the illustrated embodiment, two electrically opposite ends of the two temperature sensor units are joined together on the substrate, while the two other ends are connected to two schematically indicated conductor leads 808 that run to the outside of the furnace block 1. The two conductor leads 808 are the previously described metallic wires that are bonded to the temperature sensor units. This has the consequence that the two conductor leads 808 carry a thermoelectrical signal corresponding to the temperature difference between the sample position and the reference position. This thermoelectrical signal corresponds in a known way to the difference between the respective heat flow rates that are present on the one hand between the furnace block 801 and the sample crucible 806 and on the other hand between the furnace block 801 and reference crucible 807.

The resistance heater 802 is connected to a controlled power source (not shown in the drawing) which supplies electrical heat energy. The control is programmed in such a way that a specified dynamic temperature profile is played out as a function of time. This temperature profile is recorded with a temperature sensor 809 that is arranged in the furnace block 801 and whose output signal is carried out of the furnace block 801 through a schematically represented signal line 810. Thus, the signal line 810 carries a signal that corresponds to the specified temperature profile.

The reference symbols 811, 812 and 813 identify, respectively, a purge gas inflow conduit, a purge gas outflow conduit, and a dry gas supply conduit. Further, the reference symbols 814, 815 and 816 identify, respectively, a cooling flange, a cooling finger, and a temperature sensor. A heat barrier 817 is arranged between the cooling arrangement 814, 815 and the resistance heater 802.

In this differential calorimeter, the temperature profile to which a sample in the sample crucible 806 is exposed inside the furnace block 801 represents the excitation. The signal in the signal line 810 representing the temperature profile is recorded by a processor device with a sufficiently high update frequency. By differentiation, the time derivative of the temperature profile is calculated, whereby the heating rate is obtained. Synchronously with this process, the temperature difference signal carried by the signal line 808 is recorded which represents the differential heat flow that occurs in response to the excitation.

Although the invention has been described through the presentation of specific examples, it will be evident to the reader that numerous further variant embodiments could be developed from the teachings of the present invention, for example by combining the features of the individual embodiments with each other or by interchanging individual functional units of the individual embodiments against each other.

What is claimed is:

1. A method for manufacturing a thermoanalytical sensor for use in a thermoanalytical instrument, the method comprising the steps of:
   preparing a substrate having a top side and an underside;
   creating, on the substrate, at least one measurement position, and, for each said measurement position created, a temperature sensor unit, an electrical contact pad and a passage through the substrate, such that the passage is proximate on the substrate to the electrical contact pad, which is in electrical communication with the temperature sensor unit;
   inserting, into each passage, a metallic wire, such that an upper end of each metallic wire extends above a top end of the passage;
   melting the upper end of each metallic wire, thereby forming a metal ball at the top end of the passage; and applying pressure and heat to each formed metal ball, forming a materially integral connection between the upper end of the metallic wire and the electrical contact pad.

2. The method of claim 1, wherein the method further comprises forming two or more measurement positions and two or more temperature sensor units arranged on the substrate, wherein an individually dedicated temperature sensor unit is assigned to each measurement position.

3. The method of claim 2, wherein the temperature sensor unit is configured as a thermocouple arrangement comprising at least two thermocouples that are formed in one or more layers on the substrate.

4. The method of claim 1, further comprising the step of:
forming at least one heating resistor and at least one further electrical contact pad on the substrate, as well as forming a further passage through the sensor, wherein the heating resistor, which serves to heat the at least one measurement position, is connected by way of the electrical contact pad and a further metallic wire to an electrical power supply source, and wherein a materially integral connection in the form of a bonded joint is formed between the electrical contact pad and a metal ball that is formed at the upper end of the further metallic wire.

5. The method of claim 4, wherein thick or thin film technology is used to produce at least one of: the temperature sensor unit, the heating resistor and the electrical contact pad.

6. The method of claim 1, wherein the metallic wires include at least one of the following metals or their alloys: gold, palladium, and copper.

7. The method of claim 1, wherein the metallic wire has an approximate diameter between 0 mm and 1 mm.

8. The method of claim 7, wherein the metallic wire has an approximate diameter between 0 mm and 0.5 mm.

9. The method of claim 7, wherein the metallic wire has an approximate diameter of about 0.1 mm.

10. The method of claim 1, wherein the metal ball has a diameter of approximately 0.01 to 0.25 mm.

11. The method of claim 1, wherein the electronic circuit is configured with software so that the sensor can be used for differential scanning calorimeter measurements according to at least one of: the principle of power compensation and the heat flux principle.

12. The method of claim 1, wherein thick or thin film technology is used to produce at least one of: the temperature sensor unit and the electrical contact pad.

13. A sensor for a thermoanalytical instrument having an electronic circuit, comprising:
a substrate having a top side and an underside;
at least one measurement position, formed on the substrate; and
for each of the at least one measurement positions:
a temperature sensor unit, formed and arranged on the substrate to detect a temperature of the measurement position with which it is associated;
an electrical contact pad, formed on the top side and in electrical communication with the temperature sensor unit;
a passage through the substrate; and
a metallic wire, connected to the temperature sensor unit by way of the electrical contact pad, the metallic wire passing through the passage from the underside to the top side, where the metallic wire is terminated at an upper end thereof by a metal ball, formed by applying pressure and temperature, that provides a materially integral connection in the form of a bonded junction between the upper end of the metallic wire and the electrical contact pad, the lower end of the wire adapted for connection to the electronic circuit of the thermoanalytical instrument.

14. The sensor of claim 13, further comprising:
at least one heating resistor, formed on the substrate and arranged to heat at least one of the at least one measurement positions; and
for each of the at least one heating resistors:
an electrical contact pad, formed on the sensor and in electrical communication with the heating resistor; and
a metallic wire, in a materially integral connection with the electrical contact pad, the metallic wire in electrical communication with an electrical power supply source of the thermoanalytical instrument.

15. The sensor of claim 13, wherein:
the substrate comprises a non-conductive material selected from the group consisting of: aluminum oxide, steatite, aluminum nitrite, glass ceramics and mixtures thereof.

16. The sensor of claim 13, wherein:
the substrate comprises steel and hard metal.

17. The sensor of claim 13, wherein:
the substrate is disk-shaped.

18. The sensor of claim 13, further comprising:
a temperature sensor unit, formed and arranged on the substrate to detect an absolute temperature of the substrate.

19. The thermoanalytical instrument of claim 13, wherein the thermoanalytical instrument is configured as a differential scanning calorimeter.

* * * * *